US009857281B2

(12) United States Patent
Freitag et al.

(10) Patent No.: US 9,857,281 B2
(45) Date of Patent: Jan. 2, 2018

(54) APPARATUS AND METHOD FOR DETERMINING SIZES OF PARTICLES IN A FLUID

(71) Applicant: Siemens Aktiengesellschaft, Munich (DE)

(72) Inventors: Reinhard Freitag, Munich (DE); Robert Schrobenhauser, Munich (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 15/027,156

(22) PCT Filed: Sep. 25, 2014

(86) PCT No.: PCT/EP2014/070543
§ 371 (c)(1),
(2) Date: Apr. 4, 2016

(87) PCT Pub. No.: WO2015/049163
PCT Pub. Date: Apr. 9, 2015

(65) Prior Publication Data
US 2016/0252442 A1     Sep. 1, 2016

(30) Foreign Application Priority Data
Oct. 2, 2013   (DE) .................. 10 2013 220 004

(51) Int. Cl.
*G01N 15/02*   (2006.01)
*G01N 15/06*   (2006.01)
(Continued)

(52) U.S. Cl.
CPC ..... *G01N 15/0205* (2013.01); *G01N 15/0211* (2013.01); *G01N 15/06* (2013.01);
(Continued)

(58) Field of Classification Search
CPC .......... G01N 15/0205; G01N 15/0211; G01N 15/06; G01N 15/1436; G01N 15/1459; G01N 2015/0046; G01N 2015/0693
(Continued)

(56) References Cited

U.S. PATENT DOCUMENTS 5,056,918 A   10/1991   Bott et al. ..................... 356/336
5,085,500 A   2/1992    Blesener ....................... 356/338
(Continued)

FOREIGN PATENT DOCUMENTS

DE          69029694 T2     7/1997    ............. G01N 15/02
DE          102012211992 A1  1/2014   ............. G01N 15/00
(Continued)

OTHER PUBLICATIONS

German Office Action, Application No. 102013220004.8, 5 pages, Mar. 13, 2014.
(Continued)

*Primary Examiner* — Tri T Ton
(74) *Attorney, Agent, or Firm* — Slayden Grubert Beard PLLC

(57) ABSTRACT

An apparatus and method are provided for determining particle sizes and/or a number of particles in a fluid. The method includes emitting laser beams from a laser source, through a lens optical system having a laser absorption device, which absorbs unscattered laser beams emitted by the laser source. The laser absorption device is encompassed by first, second, and third lenses, wherein the first lens directs scattered laser beams onto the second and/or the third lens, wherein the second lens directs laser beams that impinge on the second lens proceeding from the first lens onto a first photodetector that generates first measurement signals, wherein the third lens directs laser beams that impinge on the third lens proceeding from the first lens onto
(Continued)

a second photodetector that generates second measurement signals. An evaluation device is used to evaluate the measurement signals of the two photodetectors to determine the sizes of the particles.

13 Claims, 6 Drawing Sheets

(51) Int. Cl.
    *G01N 15/00*     (2006.01)
    *G01N 15/14*     (2006.01)

(52) U.S. Cl.
    CPC ..... *G01N 15/1436* (2013.01); *G01N 15/1459* (2013.01); *G01N 2015/0046* (2013.01); *G01N 2015/0693* (2013.01)

(58) Field of Classification Search
    USPC .................................................. 356/335–343
    See application file for complete search history.

(56) References Cited

U.S. PATENT DOCUMENTS

| | | | |
|---|---|---|---|
| 5,298,968 A | 3/1994 | Cheung | 356/338 |
| 5,467,189 A | 11/1995 | Kreikebaum et al. | 356/336 |
| 6,084,670 A | 7/2000 | Yamazaki et al. | 356/343 |
| 7,053,783 B2 | 5/2006 | Hamburger et al. | 340/630 |
| 7,999,936 B1* | 8/2011 | Li | G01N 15/0205 356/336 |
| 2005/0225745 A1 | 10/2005 | Nagai | 356/73 |
| 2009/0027666 A1 | 1/2009 | Godin et al. | 356/246 |
| 2011/0019188 A1* | 1/2011 | Ray | B64D 15/20 356/342 |

FOREIGN PATENT DOCUMENTS

| | | | | |
|---|---|---|---|---|
| GB | 2041516 A | 9/1980 | | G01N 15/14 |
| WO | 2006/136147 A2 | 12/2006 | | G01N 15/14 |
| WO | 2009/100804 A1 | 8/2009 | | G08B 17/107 |
| WO | 2015/049163 A1 | 4/2015 | | G01N 15/02 |

OTHER PUBLICATIONS

International Search Report and Written Opinion, Application No. PCT/EP2014/070543, 19 pages, Jan. 8, 2015.

Chinese Office Action, Application No. 201480054549.7, 5 pages, Apr. 28, 2017.

* cited by examiner

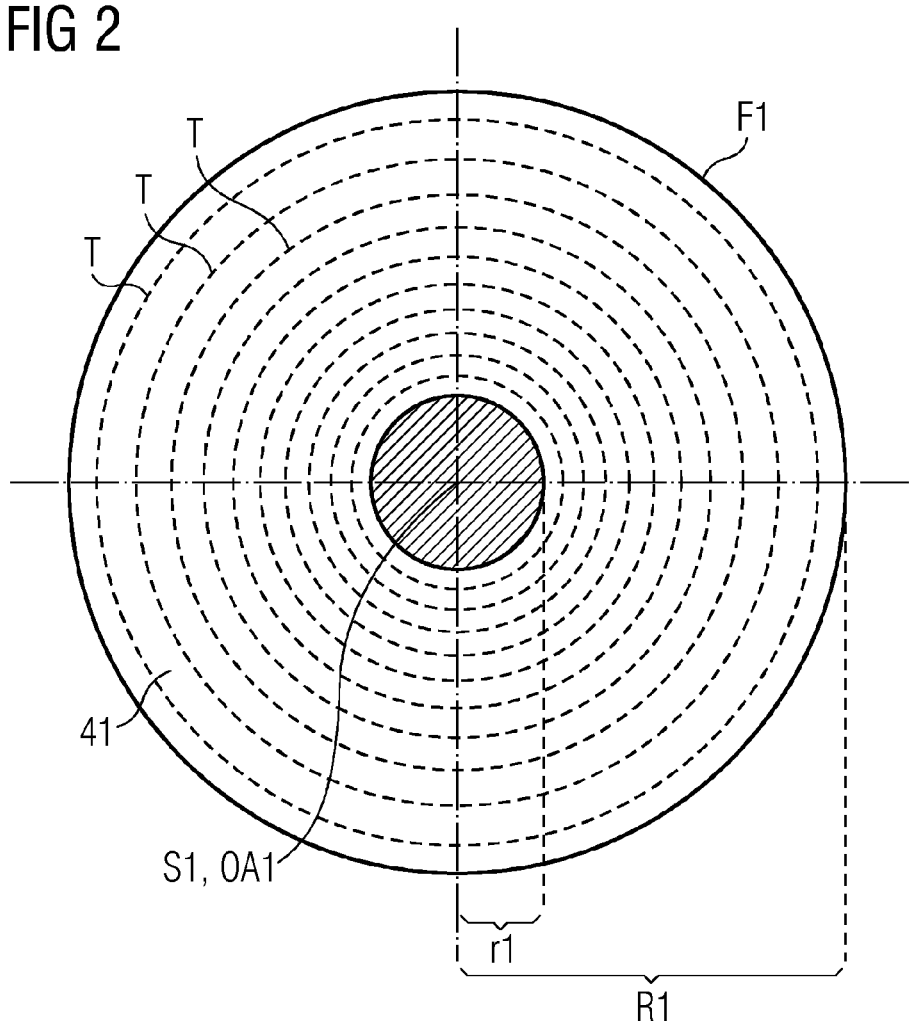

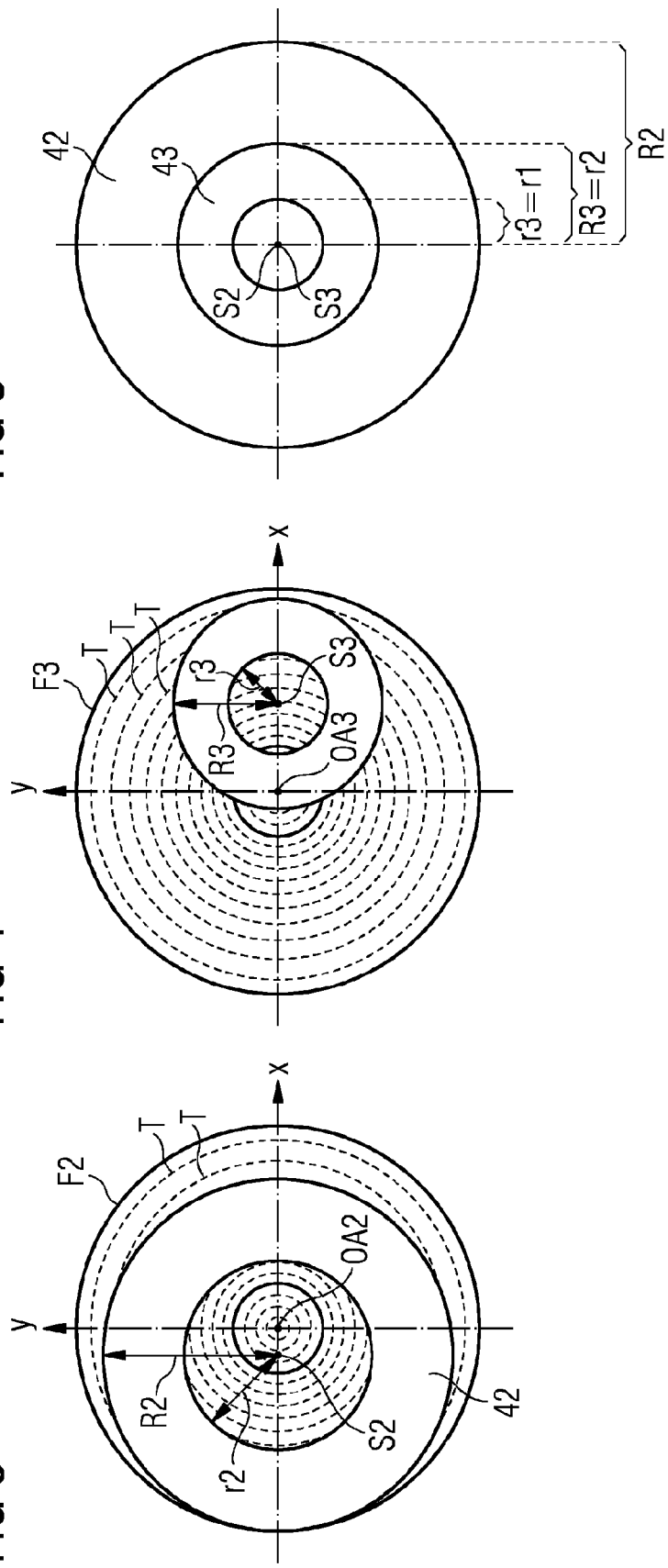

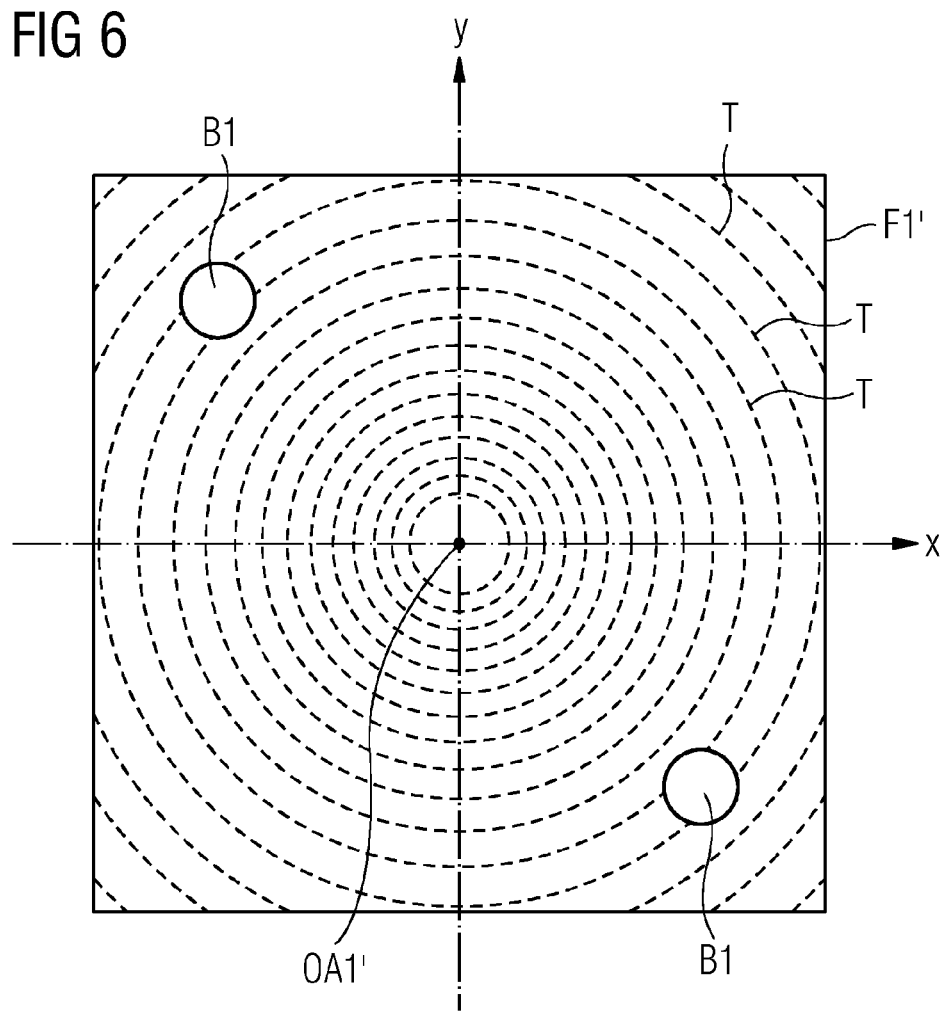

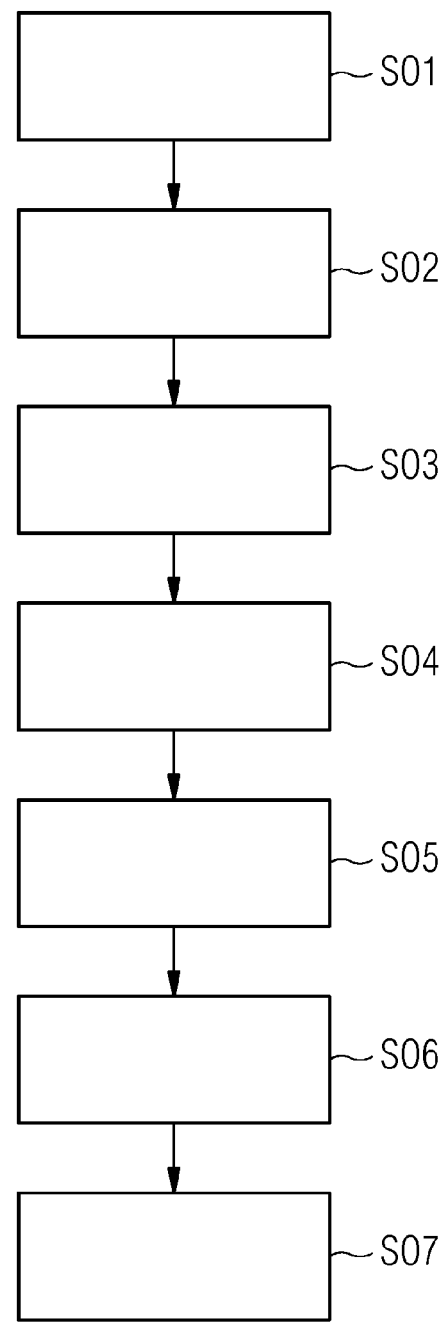

APPARATUS AND METHOD FOR DETERMINING SIZES OF PARTICLES IN A FLUID

CROSS-REFERENCE TO RELATED APPLICATIONS

This application is a U.S. National Stage Application of International Application No. PCT/EP2014/070543 filed Sep. 25, 2014, which designates the United States of America, and claims priority to DE Application No. 10 2013 220 004.8 filed Oct. 2, 2013, the contents of which are hereby incorporated by reference in their entirety.

TECHNICAL FIELD

The present invention provides an apparatus and a method for determining sizes of particles in a fluid. Furthermore, the invention provides a method for determining a number of particles in a fluid and production methods for producing the apparatus according to the invention.

BACKGROUND

Detecting particles and determining the size thereof plays a central role in many technical problems. For example, particles in a fluid can be detected before and after a filter and the size thereof can be determined, to determine an effectiveness of the filter.

In the case of laser-based detection of particles, a laser beam is coupled into the fluid, for example, a liquid, but typically a gas or gas mixture such as air, which can have the particles to be detected. The laser light can be scattered on the particles and is collected at specific angles. A signal thus arising can be measured and the particle size can be concluded therefrom, for example.

The detectable particle size can be limited by the signal-to-noise ratio (SNR). In the case of large structures, complex optical systems can be implemented to improve the signal-to-noise ratio. In applications in which the most extensive possible miniaturization is advantageous, alternative measures are taken. For example, mirrors or large-area lenses can be used to collect a larger quantity of scattered laser light.

A laser-based particle counter is described in U.S. Pat. No. 5,085,500 A, which absorbs light which is scattered by particles, which traverse a measurement volume in a fluid. To absorb the light, multiple photodetectors are arranged so that only scattered laser beams can be incident thereon. A laser beam, which is generated by a source, passes through multiple apertures to generate a laser beam having suitable properties.

SUMMARY

One embodiment provides an apparatus for determining sizes of particles in a fluid having: a lens optical system, which comprises a laser absorption device, which absorbs laser beams, which are emitted from a laser source and pass through the fluid essentially without scattering, wherein the laser absorption device is encompassed by a first lens and by a second lens and by a third lens, wherein the first lens at least partially guides laser beams, which are emitted from the laser source and are scattered on the particles in the fluid, onto the second lens and/or the third lens, wherein the second lens guides laser beams, which are incident on the second lens proceeding from the first lens, essentially onto a first photodetector, which generates first measurement signals in dependence on laser beams guided thereon, wherein the third lens guides laser beams, which are incident on the third lens proceeding from the first lens, essentially onto a second photodetector, which generates second measurement signals in dependence on laser beams guided thereon; and having an analysis device, which analyzes the measurement signals of the two photodetectors to determine the sizes of the particles.

In a further embodiment, the second lens partially encompasses the third lens.

In a further embodiment, the second lens and the third lens also encompass at least one further lens, and at least one further photodetector is provided, onto which the at least one further lens guides laser beams incident thereon.

In a further embodiment, the first lens is formed as a concentric first cutout from a first Fresnel lens and/or the second lens is formed as an eccentric second cutout from a second Fresnel lens and/or the third lens is formed as an eccentric third cutout from a third Fresnel lens.

In a further embodiment, two or three of the first Fresnel lens, the second Fresnel lens, and the third Fresnel lens are structurally identical to one another.

In a further embodiment, a holding device is formed on the laser absorption device, with which at least the first lens and the second lens are screwed together and/or adhesively bonded and the lens optical system is fixable in or on the apparatus and removable from the apparatus by means of the holding device.

In a further embodiment, a holding device of the laser absorption device, the laser absorption device, and at least the second lens and the third lens are formed as a monolithic component and the lens optical system is fixable in or on the apparatus and removable from the apparatus by means of the holding device.

In a further embodiment, the laser absorption apparatus has a beam sink having a cavity open in the direction of the laser source, into which the laser beams, which pass through the fluid essentially without scattering, enter.

In a further embodiment, the apparatus includes a measurement chamber, through which the fluid can be conducted; a detector chamber, in which the first photodetector and the second photodetector are provided; and a laser source, which generates the laser beams, wherein the laser beams are oriented through the measurement chamber onto the laser absorption device of the lens optical system, wherein the lens optical system is arranged between the measurement chamber and the detector chamber.

In a further embodiment, the first lens and the laser absorption apparatus are fluidically sealed in such a manner that the fluid cannot enter the detector chamber proceeding from the measurement chamber; and the first lens and the laser absorption apparatus are furthermore fluidically sealed in such a manner that the measurement chamber has homogeneous fluidics.

Another embodiment provides a method for determining sizes of particles in a fluid having the following steps: coupling laser beams into the fluid; deflecting laser beams, which are scattered on the particles in the fluid, by means of a first lens at least partially onto a second lens and/or a third lens; guiding laser beams, which are incident on the second lens proceeding from the first lens, by means of the second lens onto a first photodetector; guiding laser beams, which are incident on the third lens proceeding from the first lens, by means of the third lens onto a second photodetector; generating first measurement signals by means of the first photodetector in dependence on laser beams guided thereon;

generating second measurement signals by means of the second photodetector in dependence on laser beams guided thereon; and analyzing the measurement signals of the two photodetectors to determine the sizes of the particles.

In a further embodiment, the first and second measurement signals comprise items of information about light amplitudes of the laser beams guided onto the photodetectors; and the analysis of the measurement signals to determine the sizes of the particles is performed based on the Mie theory.

Another embodiment provides a method for determining a number of particles in a fluid, wherein the method disclosed above for determining the size of the particles in the fluid is carried out continuously within a period of time; wherein a counter is increased by one upon each determination of the size of one of the particles if the respective determined size of the particle exceeds a predetermined minimum value; and wherein the number of the particles in the fluid is determined subsequently to the period of time based on the counter and on the period of time.

Another embodiment provides a method for producing a lens optical system for an apparatus for determining sizes of particles in a fluid as disclosed above, the method having the following steps: injection molding the first lens in a first injection molding step; injection molding the second lens, the third lens, and the laser absorption apparatus in a second injection molding step; and mounting the first lens on the laser absorption apparatus.

Another embodiment provides a method for producing a lens optical system for an apparatus for determining sizes of particles in a fluid as disclosed above, the method including injection molding the first lens, the second lens, the third lens, and the laser absorption apparatus in a single injection molding step.

BRIEF DESCRIPTION OF THE DRAWINGS

Example aspects and embodiments of the present invention are explained in greater detail below with reference to the drawings, in which:

FIG. 2 shows a schematic frontal view of a first Fresnel lens to explain a shape of a first lens according to the first embodiment;

FIG. 3 shows a schematic frontal view of a second Fresnel lens to explain a shape of a second lens according to the first embodiment;

FIG. 4 shows a schematic frontal view of a third Fresnel lens to explain a shape of a third lens according to the first embodiment;

FIG. 5 shows a schematic frontal view of the second and third lens rings to explain the arrangement thereof in the apparatus according to the first embodiment;

FIG. 6 shows a schematic frontal view of a Fresnel lens to explain a lens optical system of an apparatus for determining sizes of particles in a fluid according to a second embodiment of the present invention;

FIG. 8 shows a schematic flow chart to illustrate a method for determining sizes of particles in a fluid according to a second embodiment of the present invention.

DETAILED DESCRIPTION

Figure 1:
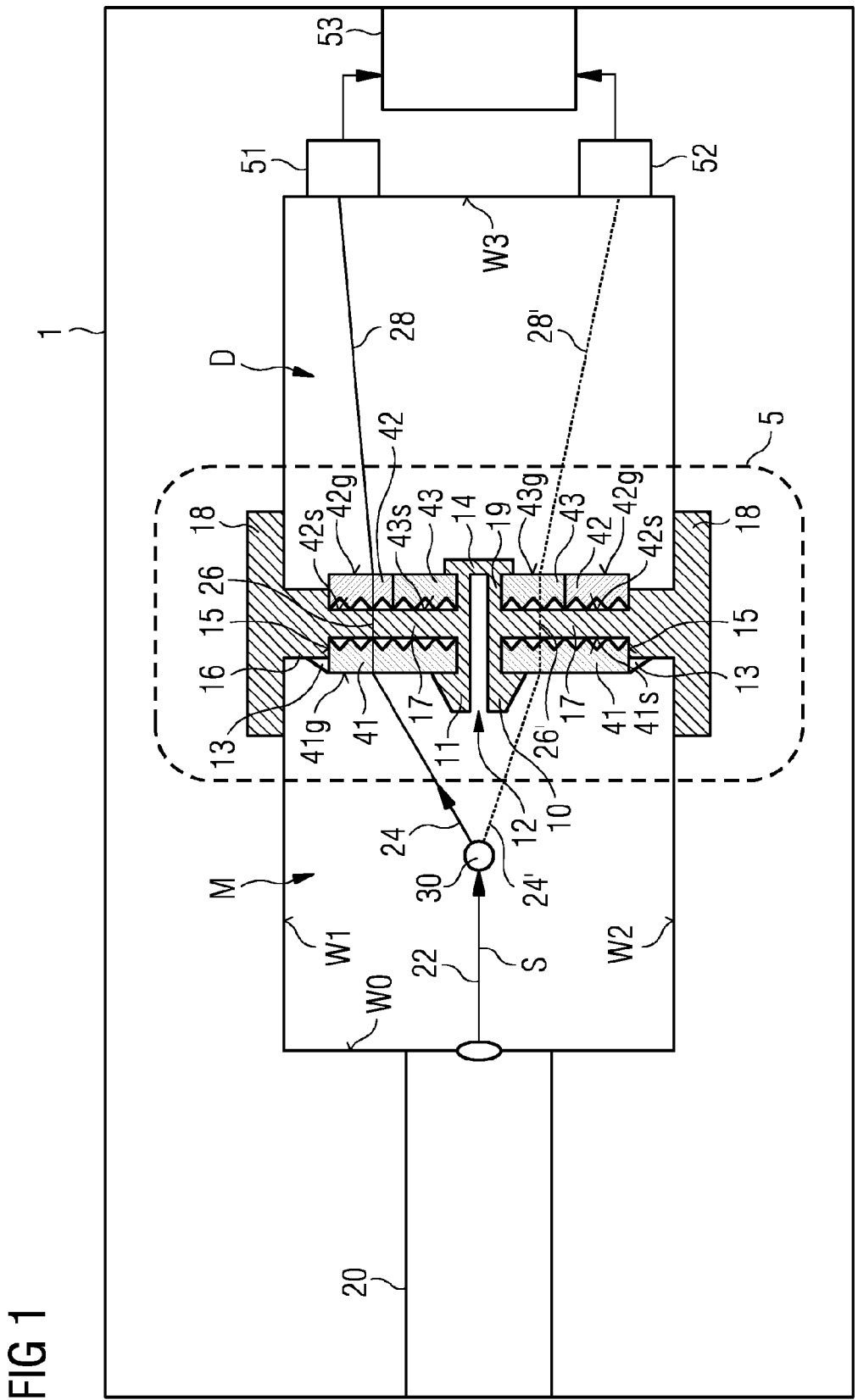
FIG. 1 shows a schematic cross-sectional view of an apparatus for determining sizes of particles in a fluid according to a first embodiment of the present invention.

Some embodiments of the present invention provide an apparatus for determining sizes of particles in a fluid, the apparatus including: a lens optical system, which comprises: a laser absorption device, which absorbs laser beams, which are emitted from a laser source and pass through the fluid essentially without scattering, wherein the laser absorption device is encompassed by a first lens and by a second lens and by a third lens, wherein the first lens at least partially guides laser beams, which are emitted from the laser source and are scattered on the particles in the fluid, onto the second lens and/or the third lens, wherein the second lens guides laser beams, which are incident on the second lens proceeding from the first lens, essentially onto a first photodetector, which generates first measurement signals in dependence on laser beams guided thereon, wherein the third lens guides laser beams, which are incident on the third lens proceeding from the first lens, essentially onto a second photodetector, which generates second measurement signals in dependence on laser beams guided thereon; and having an analysis device, which analyzes the measurement signals of the two photodetectors to determine the sizes of the particles.

Other embodiments provide a method for determining sizes of particles in a fluid having the following steps:

coupling laser beams into the fluid; deflecting laser beams, which are scattered on the particles in the fluid, by means of a first lens at least partially onto a second lens and/or a third lens;

guiding laser beams, which are incident on the second lens proceeding from the first lens, by means of the second lens onto a first photodetector;

guiding laser beams, which are incident on the third lens proceeding from the first lens, by means of the third lens onto a second photodetector;

generating first measurement signals by means of the first photodetector in dependence on laser beams guided thereon; generating second measurement signals by means of the second photodetector in dependence on laser beams guided thereon;

analyzing the measurement signals of the two photodetectors to determine the sizes of the particles.

Other embodiments provide a method for determining a number of particles in a fluid, wherein a method for determining the size of the particles in the fluid is carried out continuously within a period of time; wherein a counter is increased by one upon each determination of the size of one of the particles if the respective determined size of the particle exceeds a predetermined minimum value; and wherein the number of the particles in the fluid is determined subsequently to the period of time based on the counter and the period of time. The predetermined minimum value can in particular also be zero, that is to say that the counter is increased by each particle, the size of which is determined.

For this purpose, a flow of the fluid can be known or can be measured via a flow measuring device. Furthermore, a measurement efficiency of the method can be known, that is to say, what percentage of the particles actually located in the fluid are detected by the method on average. The counter can be modified based on the measurement efficiency, to determine an actual number of the particles located in the fluid. A concentration of the particles in the fluid can also be concluded from the flow, the counter, and the measurement efficiency.

Other embodiments provide a method for producing a lens optical system for an apparatus for determining sizes of particles in a fluid having the following steps: injection molding the first lens in a first injection molding step; injection molding the second lens, the third lens, and the laser absorption apparatus in a second injection molding step; and mounting the first lens on the laser absorption apparatus.

Other embodiments provide a method for producing a lens optical system for an apparatus for determining sizes of particles in a fluid having the following step: injection molding the first lens, the second lens, the third lens, and the laser absorption apparatus in a single injection molding step.

By arranging multiple different lenses around a central beam sink, a particularly compact and simultaneously particularly efficient lens optical system can be provided, which can be used for an apparatus for determining sizes of particles.

According to the arrangement of the second and third lenses, laser beams having different scattering angles—also on the same particle—are guided differently onto the first or the second photodetector. By measuring a light amplitude or a radiant power on each of the photodetectors, items of information can thus be obtained about the distribution of the scattering angles. For example, smaller particles can result in more scattering angles having smaller angle values than larger particles, which can result in relatively more scattering angles having larger angle values.

The implementation of the measurement, i.e., the determination of the particle sizes, by means of two items of angle information, namely one from each of the photodetectors, enables the reduction of a background signal (noise) due to random reflections of the laser light. That is to say, the signal-to-noise ratio (SNR) can be higher.

The lens optical system can be reduced in size further by the production of parts or of the entire lens optical system by means of injection molding. In addition, the production by means of an injection molding method is very precise, so that variations in the properties of optical components (for example, in the lenses) and installation inaccuracies can be minimized. Mounting and manual alignment steps can also be omitted.

In particular, the injection molding of plastics, preferably Plexiglas, can result in significant advantages with respect to production costs and production speed.

Due to the compact and simultaneously efficient embodiment, the apparatus can be used in diverse fields, for example, industry, the infrastructure branch, in building technology, environmental monitoring (for example, to measure fine dust and hyper-fine dust), or in vehicles (measuring a filter efficiency).

According to one embodiment, the second lens at least partially encompasses the third lens. "Encompasses" means in this case in particular that the third lens is inserted into a recess or a hole in the second lens or is guided through the hole. There is thus a cross-sectional plane in which the cross section through the third lens is indirectly or directly enclosed completely by the cross section of the second lens. The two lenses are therefore arranged in a particularly space-saving manner, whereby the apparatus can be miniaturized more strongly. In addition, such an arrangement is gas-tight if the second lens encloses the third lens evenly, i.e., if the hole in the third lens is completely closed by the second lens.

According to a further embodiment, the second lens and the third lens also encompass at least one further lens. At least one further photodetector can also be provided, onto which the at least one further lens guides laser beams incident thereon. If multiple further lenses are provided, in each case one lens can encompass a lens having a next-smaller external radius, so that an arrangement describable as "target-like" results. For each further lens after the third lens, a further photodetector can be provided, onto which the respective lens guides laser beams.

According to a further embodiment, the first lens is formed as a concentric first cutout from a first Fresnel lens. The first lens can image the scattered light, i.e., scattered laser beams, homogeneously, i.e., uniformly, on the second and/or third lens. The second lens can be formed as an eccentric second cutout from a second Fresnel lens.

Furthermore, the third lens can be formed as an eccentric third cutout from a third Fresnel lens. Fresnel lenses are thin, easily producible, have a high ratio of diameter to focal length, and can be calculated easily for all geometries.

Due to the eccentric cut of the second and third lenses, the laser light incident thereon is also guided eccentrically on to the photodetectors, i.e., imaged.

The eccentrically cut second lens and the eccentrically cut third lens, which is encompassed thereby, are advantageously arranged after the concentrically cut first lens in the beam direction of the coupled-in laser beam. This enables imaging of laser beams incident on the lens optical system with small imaging errors, which enables a particularly short image distance of the lens optical system. The lens optical system can thus be kept very compact, which contributes to the ability to miniaturize the apparatus.

According to a further embodiment, two or three of the first Fresnel lens, the second Fresnel lens, and the third Fresnel lens are structurally identical to one another. The calculation of the geometries can thus be simplified. In addition, the production expenditure can be reduced, because multiple different Fresnel structure molds do not have to be provided, for example, for the injection molding.

The lenses can be aligned in a confocal manner, whereby the imaging of random light of the laser, which is reflected on the laser absorption apparatus, for example, on the photodetectors can be minimized.

According to a further embodiment, a holding device is formed on the laser absorption device, with which at least the first lens and the second lens are screwed together and/or adhesively bonded. Alternatively, the first and the second lenses and/or the laser absorption device can also be adhesively bonded directly with one another.

Alternatively, a holding device of the laser absorption device, the laser absorption device, and at least the second lens and the third lens can be formed as a monolithic component. In both variants, the lens optical system can be fixable in or on the apparatus and removable from the apparatus by means of the holding device. The lens optical system can thus be replaced easily and with little technical expenditure in the event of possible soiling or damage. The first, second, and third lenses can be held in a fixed and known position in relation to or on the holding device via markings, for example, in the form of grooves or boreholes. The holding device can have counterparts corresponding to the grooves or boreholes for this purpose.

According to a further embodiment, the laser absorption apparatus has a beam sink (or: beam dump) having a cavity open in the direction of the laser source, into which the laser beams, which pass through the fluid essentially without scattering, enter.

According to a further embodiment, the apparatus has a measurement chamber, through which the fluid can be conducted;

a detector chamber, in which the first photodetector and the second photodetector are provided; and a laser source, which generates the laser beams. The laser beams are oriented through the measurement chamber onto the laser absorption device of the lens optical system. The lens optical system is arranged between the measurement chamber and the detector chamber. The laser source can comprise a laser generation device for emitting a precursor laser beam, for example, a laser-emitting diode (LED), and a laser source lens optical system, for example, for collimating the precursor laser beam into the laser beam to be scattered.

According to a further embodiment, the first lens and the laser absorption apparatus are fluidically sealed in such a manner that the fluid cannot enter the detector chamber proceeding from the measurement chamber. The optical structure, in particular the lens optical system, is gas-tight in this way. The provision of a sheath made of filtered air (so-called "sheath air") around the fluid to avoid function-disturbing particle contamination of the apparatus can therefore be unnecessary or superfluous.

Furthermore, the detector chamber, in particular the photodetectors, can thus also be protected from soiling and damage. The leak-tightness of the lens optical system enables a cleaning step of the measurement chamber to be carried out, to clean the apparatus again after measurements with a high particle concentration, for example, after a leakage of a diesel engine.

The first lens and the laser absorption apparatus can furthermore be fluidically sealed in such a manner that the measurement chamber has homogeneous fluidics. In this way, turbulence in the fluid can be avoided.

According to a embodiment of the method, the first and second measurement signals comprise items of information about light amplitudes of the laser beams guided onto the photodetectors. The analysis of the measurement signals to determine the sizes of the particles can therefore be performed based on the so-called Mie theory.

The Mie theory is the exact solution of the Maxwell equations for the scattering of an electromagnetic plane wave on a spherical object (of arbitrary size). In this case, the incident plane wave and the scattered electromagnetic field are developed into emitting spherical wave functions. The internal field is developed into regular spherical wave functions. The development coefficients of the scattered field and therefore the scattered electromagnetic field in each point in space can then be calculated via the boundary conditions on the sphere surface.

FIG. 1 shows a schematic cross-sectional view of an apparatus 1 for determining sizes of particles in a fluid according to a first embodiment of the present invention.

According to the first embodiment, the apparatus 1 has a measurement chamber M and a detector chamber D, between which a lens optical system 5 is arranged. A fluid can be conducted through the measurement chamber M, which fluid moves essentially perpendicularly to the plane of the drawing of FIG. 1 through the measurement chamber M of the apparatus 1. A laser source 20, which generates laser beams 22, is provided on a side WO of the measurement chamber M opposite to the lens apparatus 5. The laser source 20 is arranged in such a manner that the laser beams 22 are coupled into the fluid, i.e., enter the fluid. The laser source 20 is furthermore oriented onto the lens optical system 5, i.e., a beam axis S of the generated laser beams 22 points at the lens optical system 5.

A laser absorption device 10 is provided in the beam path of the laser beams 22 on the lens optical system 5. That is to say, laser beams 22 which traverse the fluid essentially without scattering are incident on the laser absorption device 10, where they are absorbed. According to the first embodiment, the laser absorption device 10 is a beam sink having a cylindrical cavity 12, which points in the direction of the laser source 20, and in which the non-scattered laser beams 22 enter and in which they are absorbed. For this purpose, the cavity 12 has an opening in the direction of the laser source 20. The cavity 12 is enclosed by an essentially cylindrical section 19 of the laser absorption device 10. An axis of rotational symmetry of the cylindrical cavity 12 is identical to an axis of rotational symmetry of the cylindrical section 19 and to the beam axis S of the generated laser beams 22.

A holding device 16 is connected to the beam sink 10. The holding device 16 has two lateral sections 18, which are T-shaped in cross section, and which are stably inserted and therefore fixed in recesses in two opposing walls W1, W2 in the interior of the apparatus 1. After removal of a cover (for example, parallel to the plane of the drawing, not shown) and by pulling on the holding device 16 in a direction perpendicular to the plane of the drawing of FIG. 1, the holding device 16 can be removed from the apparatus 1, for example, if a defect exists or cleaning is to be performed.

At least one of the two T-shaped lateral sections of the holding device 16 is connected via at least one mount arm 17 to the cylindrical section 19, wherein the at least one mount arm 17 originates radially from the cylindrical section 19.

The cylindrical section 19 is encompassed by a first lens 41 on a side of the lens optical system 5 facing toward the measurement chamber M and the laser source 20. According to the first embodiment, the first lens 41 is formed as a first lens ring 41. An inner radius r1 of the first lens ring 41 is of equal size to the radius of the cylindrical section 19, so that the first lens ring 41 evenly encloses the cylindrical section 19.

An external radius R1 of the first lens ring 41 is encompassed evenly by an edge 15 of a circular recess in the holding device 16. A possible movement of the first lens ring 41 in the direction of the measurement chamber M is prevented in a formfitting manner by a truncated-cone-like thickening 11 on an end of the cylindrical section 19 facing toward the measurement chamber M. The truncated-cone-like thickening 11 tapers in the direction of the laser source 20 and encompasses the opening of the cavity 12. According to one embodiment, the thickening 11 can be attached, for example, glued, onto the cylindrical section 19 of the laser absorption device 10, after the first lens ring 41 has been attached to the cylindrical section 19.

According to the first embodiment, the first lens ring 41 is a drilled-through Fresnel lens F1, see FIG. 2. A smooth side 41g of the first lens ring 41 faces toward the laser source 20 and the measurement chamber M, while a side of the first lens ring 41, which is structured according to the Fresnel method, faces in the direction of the detector chamber D. That is to say, the first lens ring 41 is located in the forward scattering direction of the laser beams 22.

The first lens ring 41 and the laser absorption apparatus 10 are fluidically sealed in such a manner that the fluid cannot enter the detector chamber D proceeding from the measurement chamber M, that is to say, they are sealed gas-tight. For this purpose, the surface between the first lens 41 and the T-shaped lateral sections 18 of the holding device 16 is closed using a thin plate of the holding device 16, which has a circular recess, the inner edge of which represents the edges 15. Furthermore, the first lens ring 41 and the laser absorption apparatus 10 are fluidically sealed in such a manner that the measurement chamber M has homogeneous, that is to say laminar fluidics. An adhesive 13 is applied to joints between the first lens ring 41 and the laser absorption apparatus 10 for the fluidic sealing.

A second lens 42 and a third lens 43 are provided on an end of the cylindrical section 19 of the laser absorption device 10 facing toward the detector chamber D. According to the first embodiment, the second lens 42 is a second lens ring 42 and the third lens is a third lens ring 43. The third lens ring 43 encompasses the cylindrical section 19 evenly, that is to say, an inner radius r3 of the third lens ring 43 is of equal size to the radius of the cylindrical section 19. An axis of rotational symmetry S3 of the circular hole in the interior of the third lens ring 43 having the inner radius r3 is simultaneously the axis of rotational symmetry of the cylindrical section 19.

The third lens ring 43 is encompassed by the second lens ring 42. In particular, the third lens ring 43 is encompassed by the second lens ring 42 in the radial direction and can be adhesively bonded thereto. According to the first embodiment, an outer radius R3 of the third lens ring 43 is equal to an inner radius r2 of the second lens ring 42. The axis of rotational symmetry S2 of the circular hole in the second lens ring 42 having the inner radius r2 is identical to the axis of rotational symmetry of the cylindrical section 19.

A smooth surface 42g of the second lens ring 42 and a smooth surface 43g of the third lens ring 43 are coplanar and face toward the detector chamber D. The second lens ring 42 is provided with Fresnel structures on a surface 42s, which faces away from the smooth surface 42g, of the second lens ring 42. These are explained in greater detail hereafter with reference to FIG. 3. Fresnel structures are also formed on a surface 43s, which faces away from the smooth surface 43g, of the third lens ring 43. The Fresnel structures of the third lens ring 43 are explained in greater detail hereafter with reference to FIG. 4.

To prevent a movement of the second or third lens ring 42, 43 in the direction of the detector chamber D, a nut-like widening 14 of the cylindrical section 19 is formed on the end of the cylindrical section 19 facing toward the detector chamber D, pressing against the smooth surface 43g of the third lens ring 43. According to one embodiment, the widening 14 can be connected, for example, adhesively bonded, to the cylindrical section 19, after the second lens ring 42 has been arranged around the cylindrical section 19.

A movement of the second and third lens rings 42, 43 in the direction of the first lens ring 41, and vice versa, can be prevented by the mount arms 17. The mount arms 17 separate, that is to say space apart, the surfaces 41s, 42s, 43s, which are structured according to the Fresnel method, of the lens rings 41, 42, 43 from one another. The mount arms 17 are advantageously formed particularly thin in the axial direction of the cylindrical section 19. That is to say, the surfaces 41s, 42s, 43s, which are structured according to the Fresnel method, of the lens rings 41, 42, 43 are advantageously located particularly close to one another. In embodiments, according to which no mount arms 17 are formed, the surfaces 42s, 43s can also press directly against the surface 41s, as long as the respective Fresnel structures T are not thus damaged.

The mount arms 17 are advantageously also formed particularly narrow in the tangential direction of the cylindrical section 19. Therefore, only a small fraction of the laser beams 26, 26', which are deflected by the first lens ring 41, are incident on the mount arms 17, instead of being guided in the direction of the second and third lens rings 42, 43. In other words, it is advantageous if the smallest possible surface section between the measurement chamber M and the detector chamber D is concealed by the mount arms 17.

The first, second, and third lens rings 41, 42, 43 and/or the laser absorption apparatus 10 having the holding device 16 can be produced from different materials. They are advantageously produced from the same material. The material can be a plastic, for example. Production from PMMA (Plexiglas) provides the individual components with a high resistance to greatly varying chemical substances.

The entire lens optical system 5 can be manufactured in a single injection molding step, for example, by injection molding a plastic. By using the same material for all components of the lens optical system 5, problems due to tensions, for example, due to heating, are reducible. In addition, the lens optical system 5 can be replaced easily and cost-effectively by pulling and/or pushing in a direction perpendicular to the plane of the drawing of FIG. 1, if the lens optical system 5 should be damaged or strongly soiled.

During manufacturing of the lens optical system 5 as a part of an injection molding technology/molding technology or rapid prototyping, the mount arms 17 can optionally be omitted, because the first, second, and third lens rings 41, 42, 43 can be fixedly or monolithically connected to one another via other regions of the laser absorption device 10. All components of the lens optical system 5 except for the first lens ring 41 can also be monolithically produced in one molding step, for example, an injection molding step, wherein the first lens ring 41 can subsequently be adjusted and mounted, for example, by an aligning groove. This can be advantageous, for example, if the first, second, and/or third lens rings 41, 42, 43 are formed as a cutout of an aspherical Fresnel lens.

According to the first embodiment, a first photodetector 51 and a second photodetector 52 are furthermore formed on an inner wall W3 of the detector chamber D. The inner wall W3 of the detector chamber D faces toward the lens optical system 5 and the light source 20 located behind it. The first and the second photodetectors 51, 52 are formed at an equal radial distance from the axis of rotational symmetry of the cylindrical section 19 of the laser absorption device 10, which simultaneously corresponds to the beam axis S of the non-scattered laser beams 22.

The photodetectors 51, 52 can be, for example, avalanche photodiodes. The photodetectors 51, 52 are designed to measure light amplitudes, i.e., radiant powers of laser beams 28, 28', which are incident on the photodetectors. Based on the measured light amplitudes, the first photodetector 51 generates first measurement signals and the second photodetector 52 generates second measurement signals.

The two photodetectors 51, 52 are coupled to an analysis device 53, which analyzes the measurement signals of the two photodetectors 51, 52. For this purpose, a database can be formed in the analysis device 53, which contains reference patterns and/or criteria, on the basis of which the measurement signals can be classified. On the basis of the classification, the particles which have caused the corresponding measurement signals can be classified into size classes. For example, particles which cause a light amplitude ratio between a first and a second value can be classified into a first size class, and particles which cause a light amplitude ratio between the second value and a third value can be classified into a second size class, and so on.

For this purpose, for example, a ratio of the measured light amplitudes can be formed. Particles of different sizes result in different ratios of the light amplitudes.

Based on the so-called Mie theory, the size of the particles, on which the laser beams were scattered, can be inferred from such ratios.

Furthermore, two exemplary beam paths are shown in FIG. 1. During the operation of the apparatus 1, the laser beams 22 incident on particles 30 generate a plurality of scattered laser beams 24, 24', which can be incident at different angles, in relation to the original beam direction of the generated laser beams 22, on the first lens ring 41.

The scattered laser beam 24 is incident on the smooth surface 41g of the first lens ring 41 and is deflected thereby. The laser beam 26 deflected in this manner is guided onto the second lens ring 42, by which it is in turn deflected. This further deflected laser beam 28 is guided onto the first photodetector 51, where it is measured—together with all further laser beams 28 incident on the first photodetector 51.

The further scattered laser beam 24' is incident on the first lens ring 41 in such a manner that it is guided as the deflected laser beam 26' onto the third lens ring 43. The third lens ring 43 guides the deflected laser beam 26' as the further deflected laser beam 28' onto the second photodetector 52, where it is measured—together with all further laser beams 28' incident on the second photodetector 52.

The laser beams which are scattered on the particles 30 can be classified into four categories, depending on how large the angles are, at which they are deflected from the beam axis S. If they are deflected not at all or only slightly, they are incident on the laser absorption apparatus 10. If they are deflected at somewhat larger angles, they are finally guided in a majority onto the second photodetector 52. If they are deflected at still larger angles, they are finally guided in a majority onto the first photodetector 51. If they are deflected at even greater angles, for example, 90° or more, they are no longer incident on the lens optical system 5, but rather on the inner walls W1, W2 of the measurement chamber M, for example.

Some of the exemplary laser beams 22, 24, 24', 26, 26', 28, 28', which are shown in FIG. 1, do not lie directly in the cross-sectional plane of FIG. 1, but rather are arranged above the plane of the drawing of FIG. 1, so that they extend past the mount arms 17.

The analysis device 53 can furthermore be coupled to a control device. The control device can, for example, based on the results of the analysis device 53, control a stream of the fluid. For example, in the event of exceeding or falling below specific limiting values, the stream of the fluid through the measurement chamber M can be increased or reduced, for example, by opening or closing a flap designed for this purpose. The control device can therefore be used for the purpose, for example, of generating a fluid stream having an essentially constant number of the particles 30 per unit of time.

A recording device can also be connected to the analysis device 53, which can systematically record and store the results of the analysis device 53.

FIG. 2 shows a schematic frontal view of a first Fresnel lens F1 to explain a shape of a first lens according to the first embodiment.

FIG. 2 shows in particular a schematic frontal view of a first Fresnel lens F1 having a plurality of Fresnel structures T. The first Fresnel lens F1 is rotationally symmetrical about a first optical axis OA1. The first lens 41 according to the first embodiment of the present invention is formed as if a circular disk were cut concentrically out of the first Fresnel lens F1. "Concentrically" means in this case that an axis of rotational symmetry S1 of the cut-out circular disk is identical to the optical axis OA1 of the untreated first Fresnel lens F1. The first lens ring 41 therefore has an inner radius r1, which corresponds to the radius of the cut-out circular disk. An external profile, in particular an outer radius R1 of the first lens ring 41, corresponds to an external profile, in particular the radius, of the first Fresnel lens F1.

FIG. 3 shows a schematic frontal view of a second Fresnel lens to explain a shape of a second lens 42 according to the first embodiment.

According to the first embodiment, the second lens 42 is formed as if it were an eccentric ring-shaped cutout from a second Fresnel lens F2. "Eccentric" means in this case that an axis of rotational symmetry of the circular hole in the second lens ring 42 is offset in parallel in relation to an optical axis OA2 of the second Fresnel lens F2. According to the first embodiment, the second Fresnel lens F2 is structurally identical to the first Fresnel lens F1 and therefore also rotationally symmetrical about its optical axis OA2. As a result, the eccentric cut-out second lens ring 42 is not rotationally symmetrical because of the formed Fresnel structures T, because it does not have a rotationally-symmetrical surface. An inner radius r2 of the second lens ring 42 is smaller than an outer radius R2 of the second lens ring, which is in turn smaller than a radius of the second Fresnel lens F2.

FIG. 4 shows a schematic frontal view of a third Fresnel lens to explain a shape of a third lens 43 according to the first embodiment.

According to the first embodiment, the third lens 43 is formed as if it were an eccentric ring-shaped cutout from a third Fresnel lens F3. The third Fresnel lens F3 is rotationally symmetrical about its optical axis OA3 and is furthermore structurally identical to the first and the second Fresnel lenses F1, F2. The axis of rotational symmetry S3 of the circular hole in the interior of the third lens ring 43 is offset in parallel with respect to the optical axis OA3 of the third Fresnel lens F3 and is furthermore offset in parallel with respect to the axis of rotational symmetry S2 of the circular hole in the interior of the second lens ring 42, if the second lens ring 42 were projected in accordance with its location in the second Fresnel lens F2 onto the third Fresnel lens F3.

In particular, according to the first embodiment, the second axis of rotational symmetry S2 and the third axis of rotational symmetry S3 are offset in opposite directions to one another in relation to the optical axes OA2, OA3 of the second and third Fresnel lenses F2, F3. For example, if the optical axes OA2, OA3 were situated in the origin of a Cartesian coordinate system, the second axis of rotational symmetry S2 would be offset in parallel on the negative x axis, for example, while the third axis of rotational symmetry S3 would be offset in parallel on the positive x axis.

Alternatively, it would also be conceivable that the second and third axes of rotational symmetry S2, S3 enclose an angle other than 180° with the optical axis OA2, OA3 as the vertex. Angles between 90° and 270°, in particular between 135° and 225°, are particularly advantageous. The positions of the cutouts from the Fresnel lenses F2, F3 can be based on the arrangement of the photodetectors 51, 52 in the detector chamber D, because the eccentricity of the second or third lens ring 42, 43 also determines—in addition to the Fresnel structures T—how strongly a laser beam incident on the corresponding lens ring 42, 43 is deflected.

According to the first embodiment, an inner radius r3 of the circular hole in the interior of the third lens ring 43 is smaller than an outer radius R3 of the third lens ring, which is in turn smaller than a radius of the third Fresnel lens F3.

Furthermore, the outer radius R3 of the third lens ring 43 is essentially equal to the inner radius r2 of the second lens ring 42.

FIG. 5 shows a schematic frontal view of the second and third lens rings to explain the arrangement thereof in the apparatus according to the first embodiment.

FIG. 5 illustrates that, according to the first embodiment, the second lens ring 42 encompasses the third lens ring 43 evenly. The third lens ring 43 thus lies within the circular hole within the second lens ring 42. The second axis of rotational symmetry S2 lies precisely on the third axis of rotational symmetry S3. The first, second, and/or third lens rings 41, 42, 43 could also be formed as oval rings. In the preceding description, the axes of rotational symmetry S2, S3 would then be suitable for replacement by, for example, perpendiculars on the geometric focal points of ellipsoidal holes within the second or third lens ring 42, 43, respectively. An outer circumference of the third lens ring 43 can also press evenly against an inner circumference of the second lens ring 42 with elliptical or oval lens rings 41, 42, 43. The holding device 16 also only has to be slightly changed.

The descriptions with reference to preceding FIGS. 2, 3, 4, 5 are used to describe the shapes of the lens rings 41, 42, 43. It is to be understood in particular that the corresponding lens rings 41, 42, 43 do not actually necessarily have to be physically cut out of Fresnel lenses F1, F2, F3. Instead, the lens rings 41, 42, 43 can advantageously be produced in finished form by injection molding.

If two or more lens rings 41, 42, 43 are rigidly connected to one another, they can be produced in a joint injection molding step. In particular, for example, the arrangement shown in FIG. 5, wherein the second lens ring 42 encompasses the third lens ring 43 evenly, can be produced using a single mold in a single injection molding step. The division into a second and a third lens ring 42, 43 is therefore only used for the description in this case and does not mean any actual physical separation of components.

FIG. 6 shows a schematic frontal view of a Fresnel lens to explain a lens optical system of an apparatus for determining sizes of particles according to a second embodiment of the present invention.

The second embodiment is a variant of the first embodiment and differs therefrom essentially only by way of the design of the lens optical system.

According to the second embodiment, the first Fresnel lens F1' has a rectangular, in particular a square outer profile. In addition, a borehole B1 is embodied in each case in two corners of the first Fresnel lens F1', which are diametrically opposite with respect to the optical axis OA1' of the first Fresnel lens F1'. The boreholes B1' extend perpendicularly to the first Fresnel lens F1', i.e., in parallel to the optical axis OA1'.

As in the first embodiment, the first lens 41 is formed as if a circular disk had been concentrically cut out of the first Fresnel lens F1'. Therefore, the first lens also has the rectangular, in particular square outer profile and the two boreholes B1, which are diametrical with respect to the cut-out circular disk.

According to the second embodiment, the second and third lenses are furthermore each cut out eccentrically from Fresnel lenses differently, which are structurally identical to the first Fresnel lens F1', similarly as was already described with reference to FIGS. 3 and 4. Therefore, the second lens also has the rectangular, in particular square outer profile and the two boreholes B1, which are diametrical with respect to the cut-out circular disk.

The third lens according to the second embodiment is essentially identical to the third lens 43 according to the first embodiment, because the outer profile of the Fresnel lens does not have an effect on the third lens.

Figure 7:
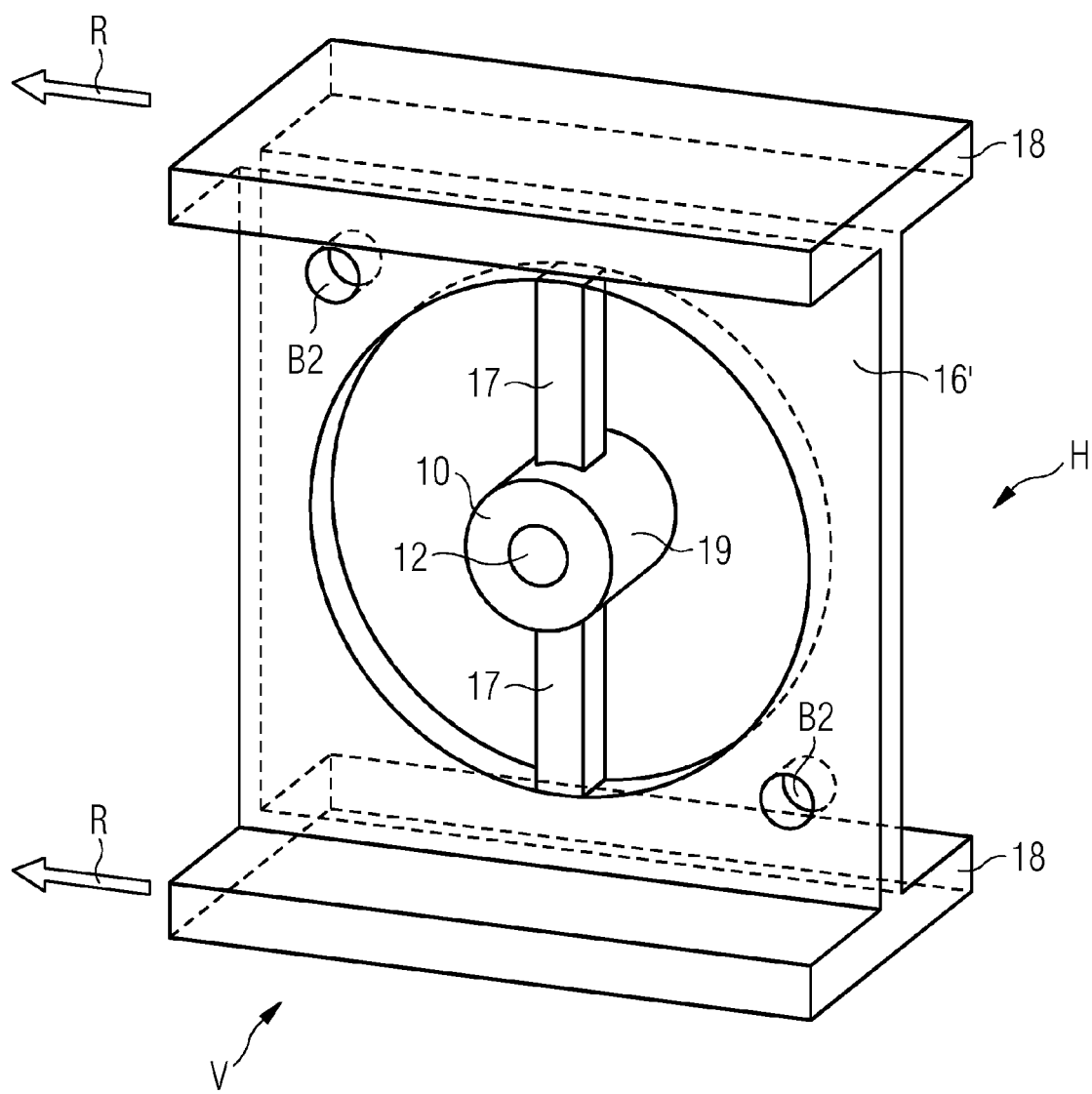
FIG. 7 shows a schematic diagonal view of a laser absorption apparatus of the apparatus for determining sizes of particles in a fluid according to the second embodiment.

FIG. 7 shows a schematic diagonal view of a laser absorption device 10 of a lens optical system 5 of the apparatus 1 for determining sizes of particles according to the second embodiment.

According to the second embodiment, the holding device 16' formed on the laser absorption device 10 has an H-shaped cross section, which is formed by pressing the two T-shaped lateral sections 18 against one another along the vertical strokes in the corresponding "Ts". Along a direction R, the holding device 16' can be inserted into the remainder of the apparatus 1, as described with reference to FIG. 1. In this case, cuboid recesses in the opposing walls W1, W2 enclose the T-shaped lateral sections 18 evenly.

A thin plate P is formed between the T-shaped lateral sections 18, corresponding to the cross stroke of the "H" in the H-shaped cross section. A circular opening F is located in the thin plate P, the axis of rotational symmetry of which is located in the middle between the two T-shaped lateral sections. In particular, the axis of rotational symmetry of the opening F is simultaneously the axis of rotational symmetry of the cylindrical section 19. The two mount arms 17 lie coplanar, are of equal thickness to the thin plate P, and each extend from opposing edge sections of the opening F up to the cylindrical section 19.

Boreholes B2 are provided in diametrically opposing corners of the plate P, which are equal in diameter to the boreholes B1 in the first Fresnel lens F1'. The truncated-cone-like thickening 11 and the nut-like widening 14 of the laser absorption apparatus are not shown for reasons of comprehensibility in FIG. 7. They can optionally be provided.

According to the second embodiment, the third lens is encompassed by the second lens, as described with reference to FIG. 5 for the second and third lens rings 42, 43 according to the first embodiment. The first lens is laid from a direction V, which is perpendicular to the thin plate P, on the thin plate P, so that one borehole B1 and B2 lies aligned on one another in each case. The second lens and the third lens are laid on the thin plate P from a direction H, which is opposite to the direction V, so that one borehole B1 and B2 lies aligned on one another in each case. The first lens, the second lens, and the interposed plate P are connected to one another, for example, screwed together, through the aligned boreholes B1, B2, B1.

FIG. 8 shows a schematic flow chart to illustrate a method for determining sizes of particles in a fluid according to a further aspect of the present invention.

The laser beams 22 are coupled into the fluid in a first method step S01.

In a step S02, the laser beams 24, which are scattered on the particles 30 in the fluid, are guided by means of the lens 41 at least partially onto a second lens 42 and/or a third lens 43. "At least partially" means in particular that not all laser beams 20 scattered on the particles 30 in the fluid are necessarily incident on the first lens 41.

In a step S03, the laser beams 26, which are incident on the second lens 42 proceeding from the first lens 41, are guided by means of the second lens 42 essentially in the direction of the first photodetector 51. Furthermore, in a step S04, laser beams 26', which are incident on the third lens 43 proceeding from the first lens 41, are guided by means of the third lens 43 onto the second photodetector 52.

In a step S05, first measurement signals are generated by means of the first photodetector 51 in dependence on the laser beams 28 guided thereon.

In a step S06, second measurement signals are generated by means of the second photodetector 52 in dependence on the laser beams 28' guided thereon.

The generated measurement signals are analyzed in a step S07 to determine sizes of particles 30, as explained in greater detail above, in particular with reference to FIG. 1.

Although the present invention was described above on the basis of exemplary embodiments, it is not restricted thereto, but rather is modifiable in manifold ways. In particular, the invention may be changed or modified in manifold ways, without deviating from the core of the invention.

For example, a fourth or multiple further lenses can additionally also be used, wherein the second lens encompasses the third lens, the third lens encompasses the fourth lens, and so on. The fourth and the multiple further lenses can also be eccentric cutouts from Fresnel lenses. However, some or all of the first, second, third, fourth, and multiple further lenses can also be eccentric or concentric cutouts from Fresnel lenses or from other lens types.

Multiple photodetectors can also be provided accordingly, wherein the fourth lens guides laser beams onto a third photodetector, a fifth lens guides laser beams onto a fourth photodetector, and so on.

What is claimed is:

1. An apparatus for determining sizes of particles in a fluid, the apparatus comprising:
   a lens optical system including a laser absorption device configured to absorb laser beams that are emitted from a laser source and pass through the fluid essentially without scattering,
   wherein respective portions of the laser absorption device are at least partially encompassed by a first lens, a second lens, and a third lens,
   the second lens radially surrounds the third lens and is adhesively bonded thereto,
   wherein the first lens at least partially guides laser beams, which are emitted from the laser source and scattered on the particles in the fluid, onto at least one of the second lens or the third lens,
   wherein the second lens guides laser beams, which are incident on the second lens proceeding from the first lens, onto a first photodetector that generates first measurement signals based on laser beams guided thereon,
   wherein the third lens guides laser beams, which are incident on the third lens proceeding from the first lens, onto a second photodetector that generates second measurement signals based on laser beams guided thereon; and
   an analysis device configured to analyze the measurement signals of the first and second photodetectors to determine sizes of the particles.

2. The apparatus of claim 1, wherein:
   the second lens and the third lens also encompass at least one further lens, and
   the apparatus includes at least one further photodetector onto which the at least one further lens guides laser beams incident thereon.

3. The apparatus of claim 1, wherein at least one of:
   the first lens
   the second lens, or
   the third lens is formed as a cutout from a Fresnel lens.

4. The apparatus of claim 3, wherein the first lens, the second lens, and the third lens are formed as a cutout of respective Fresnel lenses and at least two of the first Fresnel lens, the second Fresnel lens, and the third Fresnel lens are structurally identical to one another.

5. The apparatus of claim 1, further comprising a holding device formed on the laser absorption device, the holding device being configured to hold the first lens and the second lens together by a screwed or adhesively bonded connection, and
   wherein the holding device is configured to removably couple the lens optical system to the apparatus.

6. The apparatus of claim 1, wherein:
   a holding device of the laser absorption device, the laser absorption device, and at least the second lens and the third lens are formed as a monolithic component, and
   the holding device is configured to removably couple the lens optical system to the apparatus.

7. The apparatus of claim 1, wherein the laser absorption apparatus has a beam sink having a cavity open in a direction of the laser source, the beam sink being arranged to receive the laser beams that pass through the fluid essentially without scattering.

8. The apparatus of claim 1, comprising:
   a measurement chamber through which the fluid can be conducted;
   a detector chamber in which the first photodetector and the second photodetector are provided; and
   a laser source that generates the laser beams, wherein the laser beams are oriented through the measurement chamber onto the laser absorption device of the lens optical system,
   wherein the lens optical system is arranged between the measurement chamber and the detector chamber.

9. The apparatus of claim 8, wherein:
   the first lens and the laser absorption apparatus are fluidically sealed such that the fluid cannot enter the detector chamber proceeding from the measurement chamber; and
   the first lens and the laser absorption apparatus are furthermore fluidically sealed such manner that the measurement chamber has homogeneous fluidics.

10. A method for determining sizes of particles in a fluid, the method comprising:
    coupling laser beams into the fluid;
    deflecting laser beams, which are scattered on the particles in the fluid, by a first lens at least partially onto at least one of a second lens or a third lens;
    guiding laser beams, which are incident on the second lens proceeding from the first lens, by the second lens onto a first photodetector;
    guiding laser beams, which are incident on the third lens proceeding from the first lens, by the third lens onto a second photodetector;
    generating first measurement signals by the first photodetector based on laser beams guided thereon;
    generating second measurement signals by the second photodetector based on laser beams guided thereon; and
    analyzing the measurement signals of the first and second photodetectors to determine sizes of the particles;
    wherein the second lens radially surrounds the third lens and is adhesively bonded thereto.

11. The method of claim 10, wherein the first and second measurement signals comprise items of information regarding light amplitudes of the laser beams guided onto the photodetectors; and wherein the analysis of the measurement signals to determine the sizes of the particles is performed based on the Mie theory.

12. The method of claim 10, further comprising:

injection molding the first lens in a first injection molding step;

injection molding the second lens, the third lens, and the laser absorption apparatus in a second injection molding step; and mounting the first lens on the laser absorption apparatus.

13. The method of claim 10, further comprising injection molding the first lens, the second lens, the third lens, and the laser absorption apparatus in a single injection molding step.

* * * * *